(12) United States Patent
Paul et al.

(10) Patent No.: US 8,187,277 B2
(45) Date of Patent: May 29, 2012

(54) TRANSLATIONAL OCCIPITAL VERTEBRAL FIXATION SYSTEM

(75) Inventors: Marc T. Paul, Memphis, TN (US); William Barry Null, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 629 days.

(21) Appl. No.: 12/272,214

(22) Filed: Nov. 17, 2008

(65) Prior Publication Data
US 2010/0125299 A1    May 20, 2010

(51) Int. Cl.
*A61B 17/56* (2006.01)
(52) U.S. Cl. .............. 606/70; 606/280; 606/71
(58) Field of Classification Search .............. None
See application file for complete search history.

(56) References Cited

U.S. PATENT DOCUMENTS

| | | | |
|---|---|---|---|
| 6,524,315 | B1 | 2/2003 | Selvitelli et al. |
| 6,547,790 | B2 | 4/2003 | Harkey, III et al. |
| 6,902,565 | B2 | 6/2005 | Berger et al. |
| 7,232,441 | B2 | 6/2007 | Altarac et al. |
| 7,303,563 | B2 | 12/2007 | Poyner et al. |
| 2002/0120268 | A1* | 8/2002 | Berger .............. 606/61 |
| 2003/0004512 | A1 | 1/2003 | Farris |
| 2004/0153070 | A1 | 8/2004 | Barker et al. |
| 2005/0240181 | A1* | 10/2005 | Boomer et al. ........... 606/61 |
| 2005/0240185 | A1* | 10/2005 | Boomer et al. ........... 606/69 |
| 2005/0288669 | A1 | 12/2005 | Abdou |
| 2006/0089644 | A1* | 4/2006 | Felix ............ 606/61 |
| 2006/0155283 | A1 | 7/2006 | Doherty et al. |
| 2006/0155284 | A1* | 7/2006 | Doherty et al. ........... 606/69 |
| 2006/0229610 | A1 | 10/2006 | Piehl |
| 2007/0118121 | A1 | 5/2007 | Purcell et al. |
| 2007/0123869 | A1* | 5/2007 | Chin et al. ........... 606/61 |
| 2007/0233119 | A1 | 10/2007 | Markworth |
| 2008/0051783 | A1 | 2/2008 | Null et al. |
| 2008/0086124 | A1* | 4/2008 | Forton et al. ........... 606/60 |
| 2008/0125781 | A1* | 5/2008 | Hoffman et al. ........... 606/69 |

FOREIGN PATENT DOCUMENTS
WO    WO 2007/041085    *    4/2007

OTHER PUBLICATIONS

International Searching Authority, ISR and Written Opinion, Jul. 5, 2010.

* cited by examiner

*Primary Examiner* — Thomas C. Barrett
*Assistant Examiner* — Melissa A Golob (57) ABSTRACT

An occipital plating system includes a fixation assembly with a plate and a coupling member extending from a respective one of opposite lateral portions of the plate. The coupling members include a channel to receive a connecting element extending from the spinal column. The coupling members are rotatable and translatable relative to the plate.

18 Claims, 4 Drawing Sheets

TRANSLATIONAL OCCIPITAL VERTEBRAL FIXATION SYSTEM

BACKGROUND

Various devices have been employed for fixation of the occiput with the cervical vertebrae. Posterior systems include a plate attached to the occiput with screw fixation. A rod extends from the plate and along the cervical vertebrae for attachment to the cervical vertebrae to provide a platform for fixation. Spanning of single or multiple levels of the cervical spine results in fixation of these levels in conjunction with the occiput.

In the cervical region, anatomical considerations can make it difficult to provide a plate that adequately fits in the space along the occiput. Furthermore, securing rods or other connecting elements to the occipital plate can be difficult. Systems for occipital and cervical stabilization are needed that provide adequate stabilization while providing an optimal fit with the occiput and vertebral anatomy. Such systems should further reduce the invasiveness and complexity of the procedure.

SUMMARY

According to one aspect, an occipital plating system includes a plate with a profile adapted for positioning on the occiput. The plate extends bi-laterally across the central axis of the spinal column to opposite lateral portions of the plate. At least one coupling member extends each of the lateral portions of the plate and is movable relative to the plate. Each of the at least one coupling members is engageable to a respective connecting element extending from the spinal column to the occiput.

According to another aspect, an occipital plating system includes a plate with a central portion extending along a medial-lateral axis between opposite lateral portions. The plate includes a top surface and a bottom surface opposite the top surface. The bottom surface is for positioning distally toward an occiput and the central portion of the plate includes at least one fastener hole extending between the top and bottom surfaces to receive a fastener therethrough to secure the plate to the occiput. The lateral portions each include a coupling member associated therewith extending proximally from the top surface, and the coupling members are each configured to engage a connecting element extending from a vertebra to the occiput. At least one of the lateral portions includes an elongated slot extending along the medial-lateral axis that opens at the top and bottom surfaces. A mounting member is secured to the at least one lateral portion and extends across the slot along the medial-lateral axis. The associated coupling member is positioned on the mounting member and the associated coupling member is translatable on the mounting member relative to the lateral portion.

According to another aspect, an occipital plating system includes a plate with a central portion extending along a medial-lateral axis between opposite first and second lateral portions. The plate further includes a top surface and a bottom surface opposite the top surface where the bottom surface is for positioning distally toward an occiput. The central portion of the plate includes at least one fastener hole extending between the top and bottom surfaces to receive a fastener therethrough. The first and second lateral portions each include a coupling member associated therewith extending proximally from the top surface, the coupling members each being configured to engage a connecting element extending from a vertebra to the occiput. The first and second lateral portions each include an elongated slot extending along the medial-lateral axis that opens at the top and bottom surfaces. First and second mounting members are secured to respective ones of the first and second lateral portions, and the first and second mounting member each extend across the slot of the respective lateral portion in a direction along the medial-lateral axis. The coupling members of the first and second lateral portions are positioned on the respective mounting member and each of the coupling members is translatable in the slot on the respective mounting member relative to the lateral portion.

These and other aspects will also be apparent from the following description and the Figures.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

Figure 1:
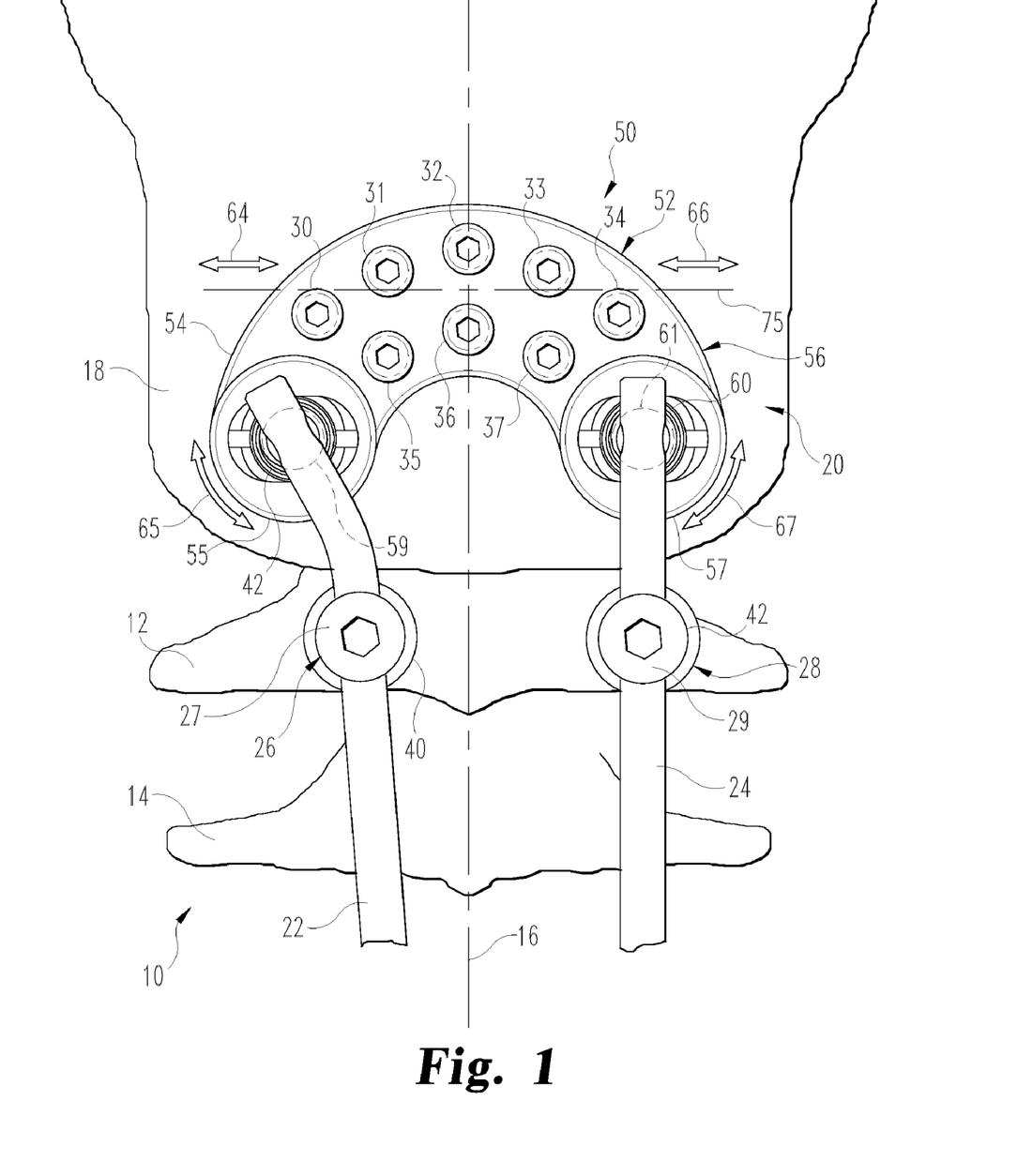
FIG. 1 shows an occipital vertebral fixation system looking cephaladly toward the occiput.

Referring to FIG. 1, there is shown a posterior elevation view of a spinal column segment 10 including the upper cervical vertebra C1 designated at 12 and the next lower cervical vertebra C2 designated at 14. Cervical vertebrae 12, 14 extend along the central axis 16 of spinal column segment 10. Occiput 18 resides at the superior end of C1 vertebra 12. Occipital fixation system 20 includes an occiput fixation assembly 50 engaged to occiput 18 and a pair of elongated connecting elements 22, 24 engaged to at least one of the cervical vertebrae 12, 14. Connecting elements 22, 24 are bi-laterally positioned along opposite sides of the spinous processes of one or more of the cervical vertebrae and central axis 16 of the spinal column, and engaged to posterior spinal elements on one or more cervical vertebrae with one or more anchors 26, 28, respectively. One or both of connecting elements 22, 24 may further extend along the spinal column to one or more of the thoracic, lumbar and sacral regions and engaged to one or more vertebrae thereof with any suitable connector.

Connecting elements 22, 24 extend along the spinal column and can be rigid to prevent motion, flexible, or partially flexible to allow at least limited motion in the stabilized motion segments. The connecting elements can be in the form of rods, plates, bars, tethers, cables, dampeners, springs, or other structure to provide a desired stabilization effect. The connecting elements 22, 24 can be secured to the vertebrae with any suitable bone anchoring device. In the illustrated embodiment, bone anchors 26, 28 are engaged to vertebra 12 and also to connecting elements 22, 24 with engaging members 27, 29 engaged to the respective bone anchors 26, 28.

The bone anchors 26, 28 can include bone screws with a receiving portion 40, 42, respectively, for receiving the respective connecting element 22, 24. The receiving portion 40, 42 can be movable relative to the bone engaging portion or fixed relative to the bone engaging portion of the respective anchoring device 26, 28. The receiving portions 40, 42 can be in the form of a top-loading, side-loading or bottom loading member with a channel to receive the respective connecting element 22, 24. Engaging members 27, 29 can be provided in the form of a set screw, nut, cap, slide-lock device, or other device can be engaged to the respective receiving portion 40, 42 to secure the connecting element 22, 24 in the respective receiving portion 40, 42. The receiving portions 40, 42 can also be in the form of a clamp, wire or other device positioned around the connecting element 22, 24 to secure it to the bone anchoring portion. The bone anchoring portion (not shown) can be in the form of a bone screw, hook, cable, anchor, staple, interbody device, clamp, or other suitable bone engaging structure to secure the respective connecting element 22, 24 to the corresponding bony structure.

Fixation assembly 50 secures at least one of the connecting elements 22, 24 to the occiput 18. Fixation assembly 50 includes a plate 52 engaged to the occiput with one or more fasteners 30, 31, 32, 33, 34, 35, 36 and 37. Fasteners 30, 31, 32, 33, 34, 35, 36, 37 can be in the form of bone screws with a threaded shaft (not shown) and a proximal head (shown) that is positioned against a proximally oriented surface of plate 52 to secure it against or adjacent to the occiput. In the illustrated embodiment, eight fasteners are shown and plate 52 includes eight holes to accommodate respective ones of the eight fasteners. It is contemplated that fewer than eight fasteners may be provided so that one or more holes do not include a fastener. Furthermore, plate 52 may be provided with fewer than eight holes or more than eight holes, and fasteners can be provided and inserted through all or a portion of the holes provided in plate 52.

When secured to the occiput, plate 52 extends transversely to the central axis 16 of the spinal column and along medial-lateral axis 75 to opposite lateral portions 54, 56. Lateral portions 54, 56 are located bi-laterally relative to central axis 16 and are offset caudally from medial-lateral axis 75 to laterally offset coupling member 58, 60 to opposite sides of the medial nuchal line and then caudally in a direction generally along central axis 16 to a respective one of the outer ends 55, 57. The laterally and caudally located outer ends 55, 57 each include a respective one of coupling members 58, 60, which extend proximally away from the occiput from the respective lateral portion 54, 56 to receive the respective connecting element 22, 24 therein. An engaging member 59, 61 (shown in phantom) such as a set screw, cap, nut or other device can be engaged to each of the coupling members 58, 60 to secure the respective connecting element 22, 24 to, in, on or around coupling members 58, 60. Alternatively, coupling members 58, 60 can be configured to crimp, clamp, frictionally lock, capture or otherwise secure the respective connecting element 22, 24 thereto without a separate engaging member.

Figure 2:
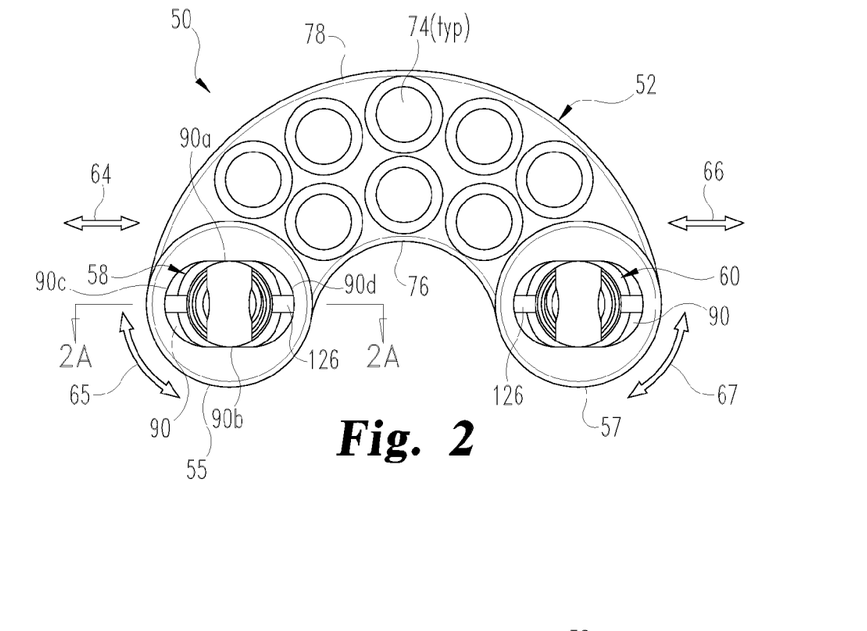
FIG. 2 shows a plan view of a fixation assembly comprising a portion of the system of FIG. 1.
Figure 3:
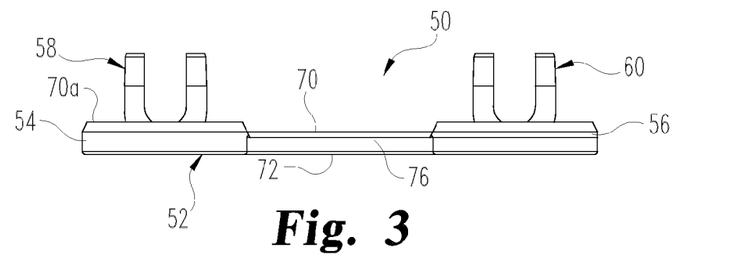
FIG. 3 is an elevation view of the fixation assembly of FIG. 2.

Referring further to FIGS. 2-3, occiput fixation assembly 50 is configured so that coupling members 58, 60 include medial-lateral adjustability along medial-lateral axis 75, as indicated by arrows 64, 66, to provide a desired fit and location of coupling members 58, 60 relative to the occipital and cervical anatomy and the connecting elements 22, 24. For example, coupling member 58 can be moved medially or laterally relative to lateral portion 54 as indicated by bi-directional arrow 64 and coupling member 60 can be moved medially or laterally relative to lateral portion 56 as indicated by bi-directional arrow 66. The independent medial-lateral adjustability of the coupling members 58, 60 relative to the respective lateral portions 54, 56 allow the spacing between coupling members 58, 60 to be increased or decreased during the surgical procedure as may be needed or desired by the surgeon to accommodate placement and engagement of the respective connecting element 22, 24.

Furthermore, coupling members 58, 60 can be independently and selectively rotated relative to the respective lateral portion 54, 56 as indicated by rotational arrows 65, 67, respectively. Rotation of coupling members 58, 60 can provide alignment of the respective coupling member 58, 60 to receive the adjacent connecting element 22, 24 extending from the cervical region of the spinal column to minimize or eliminate additional bending or contouring of the connecting element during the surgical procedure, although bending and contouring of connecting elements 22, 24 during the surgical procedure is not precluded.

Referring further to FIGS. 4-7, plate 52 includes a top surface 70 and a bottom surface 72 opposite top surface 70. Bottom surface 72 is positioned against or adjacent the bone of the occiput when plate 52 is implanted in the patient. Holes 74 extend between and open at top and bottom surfaces 70, 72. Plate 52 also includes a caudally oriented sidewall 76 extending between top and bottom surfaces 70, 72 and an opposite cephaladly oriented sidewall 78 extending between top and bottom surfaces 70, 72. Caudal sidewall 76 is concavely curved across medial-lateral axis 75 between lateral portions 54, 56 and cephalad sidewall 78 is convexly curved across medial-lateral axis 75 between lateral portions 54, 56. The concave-convex curvature provides plate 52 with a U-shaped configuration with the opening of the U shape oriented in the caudal direction when plate 52 implanted and secured to the occiput. Lateral portions 54, 56 each include a convexly curved sidewall 80, 82, respectively, that extends between and connects sidewalls 76, 78.

Figure 5:
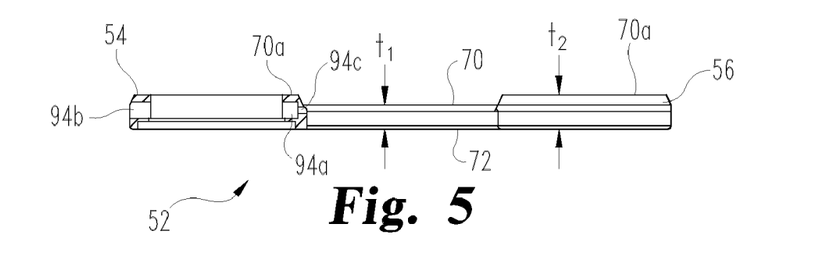
FIG. 5 is a section view through line 5-5 of FIG. 4.
Figure 6:
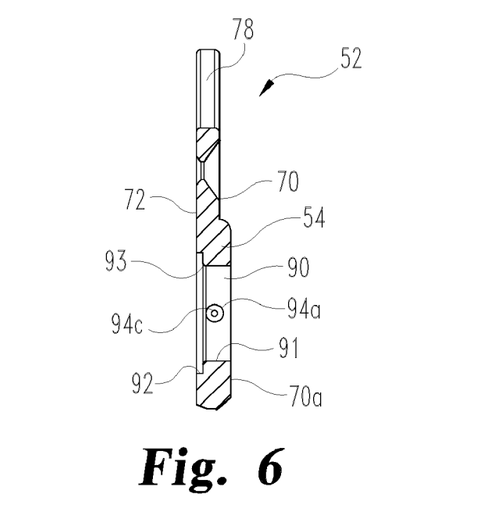
FIG. 6 is a section view through line 6-6 of FIG. 4.

Plate 52 includes a central portion 84 extending between lateral portions 54, 56. As shown in FIG. 5, central portion 84 includes a first thickness t1 between top and bottom surfaces 70, 72, and lateral portions 54, 56 include a second thickness t2 between top and bottom surfaces 70a, 72. Top surface 70a projects outwardly from top surface 70 to provide lateral portions 54, 56 with a raised profile relative to central portion 84. Holes 74 are distributed about central portion 84 with three holes 74 located adjacent to and following caudal sidewall 76 and five holes 74 located adjacent to and following cephalad sidewall 78. The three hole and five hole arrangements lie along arc axes 76a, 78a, respectively, that parallel the arc formed by the respective sidewall 76, 78. Holes 74 occupy a substantial portion of the surface area of central portion 84 and provide multiple locations and options for surgeon placement of fasteners to secure plate 52 to the occiput, while the concave-convex shape of plate 52 and hole arrangement minimize the area of the occiput occupied by plate 52. Furthermore, holes 74 provide plate 52 with flexibility so that central portion 84 can be bent and flexed to conform to the anatomy. Of course, other hole arrangements are also contemplated.

Figure 7:
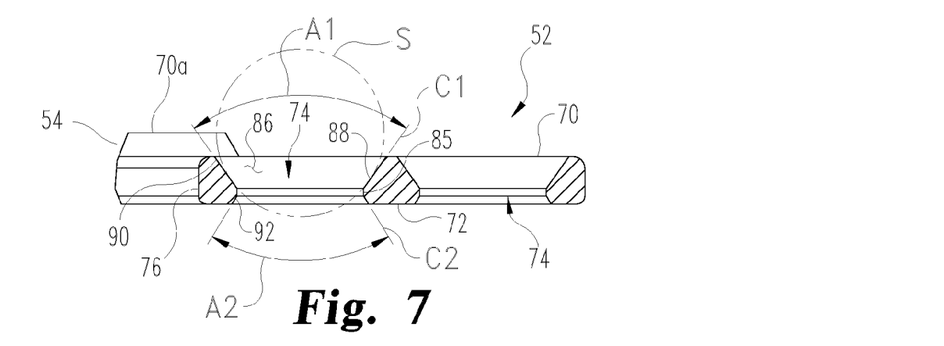
FIG. 7 is a section view through line 7-7 of FIG. 4.

As further shown in FIG. 7, each hole 74 includes a central cylindrical portion 85 orthogonally oriented to top and bottom surfaces 70, 72 of central portion 84. An upper recess 86 extends outwardly from cylindrical portion 85 to top surface 70. Upper recess 86 includes a spherical portion 88, indicated by sphere S, adjacent to and connecting with cylindrical portion 85 and an upper frusto-conically tapered portion 90, indicated by cone C1, extending outwardly from and connected to spherical portion 88 and top surface 70. Upper tapered portion 90 forms taper angle A1. The bottom of each hole 74 includes a lower frusto-conically tapered portion 92, indicated by cone C2, which extends outwardly from cylindrical portion 85 to bottom surface 72 at a taper angle A2. Cylindrical portion 85 forms the minimum size of hole 74 to prevent the bone fastener from passing therethrough, and the tapered portions and spherical portion permit the bone fastener in hole 74 to be angled relative to hole 74 and recessed into hole 74 to minimize or eliminate the protrusion of the fastener from top surface 70. It is contemplated that each hole 74 can be formed with an identical configuration through plate 52, or that one or more holes 74 include different configurations from that described above.

Fixation assembly 50 may be provided with a retaining system (not shown) to prevent one or more of the fasteners in holes 74 from backing out relative to plate 52. A retaining system can be provided for each bone engaging fastener, or a single retaining system can be provided for all bone engaging fasteners. Other suitable retaining systems are contemplated, including lock washers, caps and devices that expand the heads of the bone engaging fasteners, or plates, washers or set screws that cover or overlap the heads of one or more of the bone fasteners in holes 74. It is further contemplated that fixation assembly 50 can be provided without any retaining systems.

Figure 4:
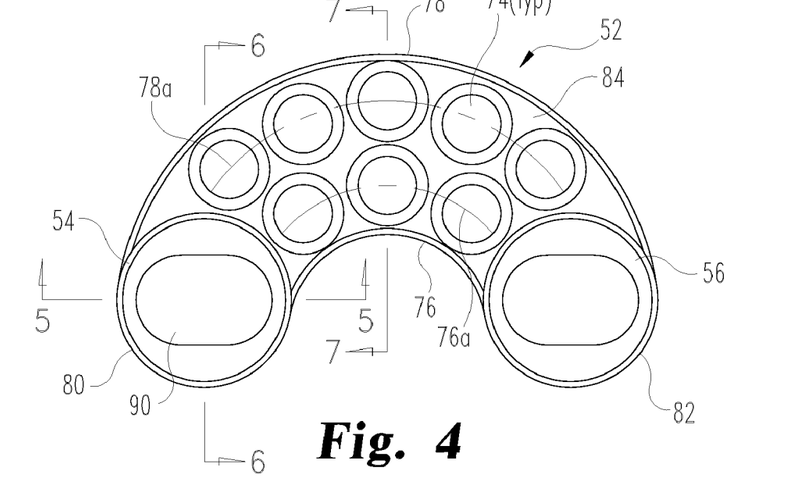
FIG. 4 is a plan view of a plate of the fixation assembly of FIG. 2.

Referring back to FIGS. 4-6, lateral portions 54, 56 will be described further with reference to lateral portion 54, it being understood that lateral portion 56 is identical to lateral portion 54, although different configurations for lateral portions 54, 56 are not precluded. Top surfaces 70a of lateral portions 54, 56 are spaced from top surface 70 to form lateral portions 54, 56 with a circular shape at the respective ends of central portion 84 when viewed from above in the proximal to distal direction as shown in FIG. 4. Lateral portions 54, 56 include an elongated slot 90 that is elongated in the direction generally parallel to medial-lateral axis 75. Elongated slots 90 extend between and open at bottom surface 72 and top surface 70a of lateral portions 54, 56. Each elongated slot 90 includes a distal recessed portion 92 adjacent to and connected to bottom surface 72 that extends outwardly from the proximal portion 91 of slot 90 to create an opening for slot 90 at bottom surface 72 that is greater in dimension than at top surface 70a. The proximal portion 91 of elongate slot 90 is connected to recessed portion 92 with chamfer 93. As shown in FIG. 5, lateral portions 54, 56 further each include a bore 94 extending in the sidewalls thereof that opens into slot 90 at the opposite lateral sides of slot 90. Bore 94 includes a first portion 94a opening into slot 90 and a second portion 94b extending between and opening through cephalad sidewall 78 and into slot 90. First portion 94a extends from slot 90 to a reduced size portion 94c that extends from first portion 94a through caudal sidewall 76.

Coupling members 58, 60 are movably coupled to respective ones of the lateral portions 54, 56 in its slot 90, and coupling members 58, 60 project proximally from top surface 70a as shown in FIG. 3 for engagement with the respective connecting element 22, 24 as shown in FIG. 1. As further shown in FIGS. 8-10, it is understood that coupling members 58, 60 are identical to one another, although providing coupling members 58, 60 in different configurations is not precluded. Coupling members 58, 60 each include a bottom flange 100 having a distal side lying in or parallel to a plane P, and a saddle 102 extending proximally from and connected to distal flange 100. In one embodiment, plane P is defined by bottom surface 72 around slot 90. In the illustrated embodiment, the distal surface of flange 100 is offset distally from and parallel to bottom surface 72 around slot 90. Plane P in another embodiment corresponds to or is parallel to the distal side of flange 100. In the illustrated embodiment, flange 100 projects radially outwardly from saddle 102 to form a circular shape with a lip 104 projecting around saddle 102. Flange 100 is positioned in recessed portion 92 of slot 90 with lip 104 contacting the respective lateral portion 54, 56 in slot 90 at the junction between proximal portion 91 and recess 92 to prevent coupling members 58, 60 from passing through top surface 70a at slot 90. As shown in FIG. 2, flange 100 contacts plate 52 along the elongated and narrowly spaced portions 90a, 90b of slot 90 when centered in slot 90, while widely spaced ends 90c and 90d of slot 90 are spaced from flange 100 to provide space for coupling members 58, 60 to translate in slot 90 between ends 90c, 90d.

Figure 8:
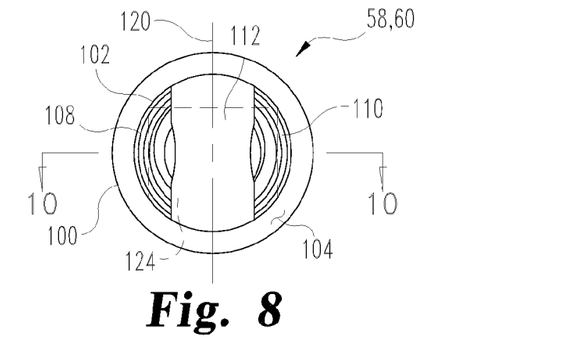
FIG. 8 is a plan view of a coupling member of the fixation assembly of FIG. 2.

Saddle 102 includes a base 106 formed monolithically with flange 100 and a pair of arms 108, 110 extending from base 106 on opposite sides of a channel 112. Arms 108 112 are located on respective ones of the lateral and medial sides 134, 136 of coupling members 58, 60. Arms 108, 110 each include an internal thread profile 114, 116, respectively, to threadingly engage the respective engaging member 59, 61 when engaged to coupling member 58, 60. Thread profiles 114, 116 extend from the top end 115, 117 of the respective arm 108, 110 to a location spaced proximally from a bottom support surface 118. Support surface 118 extends between and connects the inner surfaces of arms 108, 110 and defines a bottom support surface of channel 112 against which the respective connecting element 22, 24 is positioned. As shown in FIG. 8, channel 112 extends and opens along an axis 120 between the cephaladly and caudally oriented sides 130, 132 of coupling member 58, 60. Channel 112 also opens at the top ends 115, 117 of arms 108, 110 to allow connecting element 22, 24 to be top-loaded into channel 112. Arms 108, 110 each include a through-hole 121, 122 extending therein that opens into thread profiles 114, 116 respectively. Through-holes 121, 122 receive a tool or other device (not shown) that facilitates translation and rotation of coupling member 58, 60 in slot 90.

Figure 9:
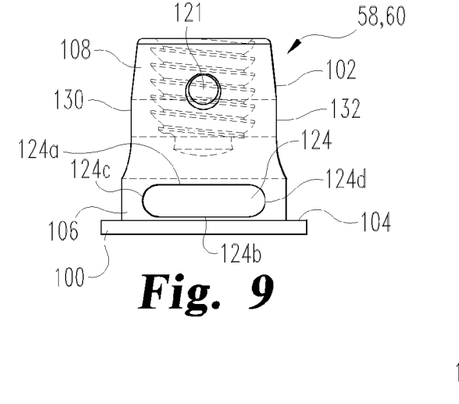
FIG. 9 is a side elevation view of the coupling member of FIG. 8.
Figure 10:
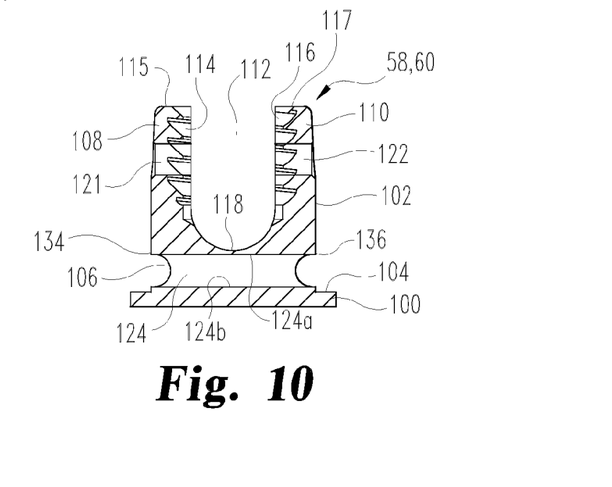
FIG. 10 is a section view along line 10-10 of FIG. 8.

As shown in FIGS. 9 and 10, base 106 includes a transverse bore 124 extending therethrough that opens at the lateral and medial sides 134, 136 of arms 108, 110. Bore 124 includes elongated proximal and distal sides 124a, 124b. Proximal and distal sides 124a, 124b are elongated in the medial-lateral direction between the lateral and medial sides 134, 136 and in the cephalad-caudal directions toward cephalad and caudal sides 130, 132 of coupling members 58, 60 so that bore 124 includes a rectangular shape when viewed from above, as shown in FIG. 8. Proximal side 124a is located adjacent to but isolated from channel 112, and distal side 124b is located adjacent to flange 100. Proximal and distal sides 124a, 124b are connected at opposite ends with curved endwalls 124c, 124d located toward the cephalad and caudal sides 130, 132.

Mounting member 126 is sized to extend through transverse bore 124 and contact proximal and distal sides 124a, 124b to maintain coupling member 58, 60 in general alignment relative to top surface 70a and bottom surface 72 of plate 52. Mounting member 126 is further sized relative to bore 124 to allow coupling members 58, 60 to be translated on mounting member 126 between opposite ends 124c, 124d of bore 124.

Figure 2A:
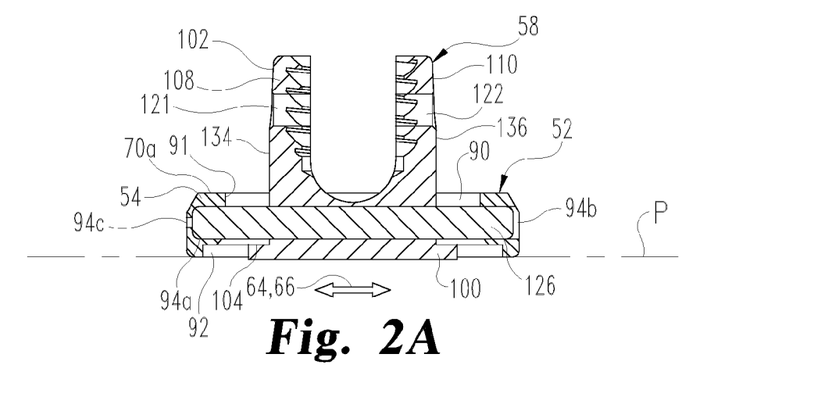
FIG. 2A is a section view along line 2A-2A of FIG. 2.

As shown in FIG. 2A, mounting member 126 is in the form of a cylindrical pin that is press fit into bore 94. The pin spans slot 90 in the medial-lateral direction along axis 75 and is received in portions 94a, 94b of bore 94. The length of mounting member 126 and slot 90 is greater than the length of bore 124, allowing coupling members 58, 60 to translate medially-laterally along mounting member 126 from one side of slot 90 to the other side of slot 90. The medial-lateral positioning of each coupling member 58, 60 is independently adjustable to adjust the medial-lateral spacing of each coupling member 58, 60 relative to central axis 16 to engage the respective connecting element 22, 24. In addition, coupling members 58, 60 are translatable by rotation about mounting member 126 while maintaining flange 100 in the same proximal-distal orientation relative to bottom surface 72. For example, flange 100 remains substantially in plane P or in a plane generally parallel to plane P during translation of coupling members 58, 60, allowing the orientation of channel 112 and its axis 120 relative to central axis 16 and medial-lateral axis 75 of each coupling member 58, 60 to be independently adjusted to receive the respective connecting element 22, 24 in channel 112 thereof.

One technique for implanting the system 20 will be described. Plate 52 can be contoured to lie along and against the occiput. Plate 52 can be placed along the median nuchal line of the occiput so that coupling members 58, 60 lie either along or lateral to the median nuchal line and bi-laterally relative to central axis 16 of the spinal column. Connecting elements 22, 24 can be positioned for engagement to coupling members 58, 60 by the surgeon during surgery and engaged thereto with, for example, engaging members 59, 61 when the desired fit for system 20 has been obtained. Connecting elements 22, 24 can be provided in straight or pre-bent configurations, and in either configuration can be positioned without further bending, or can be further bent, for engagement to coupling members 58, 60. Connecting elements 22, 24 can be pre-contoured to fit the patient's anatomy extending along the spinal column, or contoured during surgery to provide a desired custom fit with the patient.

Fixation assembly 50 is provided with an occipital plate 52 that includes a low profile both extending proximally or away from the occiput and also extending medially-laterally relative to the occiput. Fixation assembly 50 also allow the coupling members 58, 60 and connecting elements 22, 24 to be axially, medially-laterally and angularly adjusted relative to plate 52 to provide the desired fit with the patient anatomy. Placement and securing of one or more fusion devices and/or fusion material in the disc space or other location between one or more of the vertebrae along which connecting elements 22, 24 extend and its adjacent vertebrae are also contemplated. Further stabilization of one or more of the cervical vertebrae with one or more anterior plating systems is also contemplated in addition to the fixation assembly 50.

While the invention has been illustrated and described in detail in the drawings and foregoing description, the same is to be considered as illustrative and not restrictive in character. All changes and modifications that come within the spirit of the invention are desired to be protected. For example, one of coupling members 58, 60 may be fixed relative to its respective lateral portion 54, 56, or movable relative to all or a portion of plate 52 by another engagement relationship with plate 52. Also, other shapes for central portion 84 and lateral portions 54, 56 are contemplated.

What is claimed is:

1. An occipital plating system, comprising:
   plate including a central portion extending along a medial-lateral axis between opposite lateral portions, said plate further including a top surface and a bottom surface opposite said top surface, said bottom surface for positioning distally toward an occiput, said central portion of said plate including at least one fastener hole extending between said top and bottom surfaces to receive a fastener therethrough, said lateral portions each including a coupling member associated therewith extending proximally from said top surface, said coupling members each being configured to engage a connecting element extending from a vertebra to the occiput, wherein:
   at least one of said lateral portions includes an elongated slot extending along said medial-lateral axis that opens at said top and bottom surfaces;
   a mounting member is secured to said at least one lateral portion and extends across said elongated slot along said medial-lateral axis;
   said associated coupling member is positioned on said mounting member and said associated coupling member is translatable on said mounting member in said elongated slot relative to said at least one lateral portion;
   said mounting member is an elongated pin extending across said elongated slot between opposite sides of said at least one lateral portion;
   said coupling member includes a channel for receiving the connecting element and a transverse bore extending through said coupling member that is isolated from said channel; and
   said elongated pin is positioned through said transverse bore with said coupling member being slidable along said elongated pin and rotatable on said elongated pin.

2. The plating system of claim 1, wherein said plate includes: a first sidewall convexly curved across said medial-lateral axis at a cephalad end of said plate that extends between said top and bottom surfaces of said plate; and a second sidewall concavely curved across said medial-lateral axis at a caudal end of said plate that extends between said top and bottom surfaces of said plate.

3. The plating system of claim 2, wherein said lateral portions of said plate each include a convexly curved sidewall extending between said convexly curved sidewall and said concavely curved sidewall.

4. The plating system of claim 3, wherein said top surface extends along said central portion of said plate and said lateral portions each include a second top surface that is spaced from said top surface of said central portion of said plate, said lateral portions each including a thickness between said bottom surface of said plate and said second top surface that is greater than a thickness of said central portion between said bottom surface of said plate and said top surface of said central portion.

5. The plating system of claim 4, wherein said second top surfaces each form a circular shape at respective ends of said central portion when said plate is viewed in a direction from said top surface toward said bottom surface.

6. The plating system of claim 2, wherein said at least one hole includes three holes through said central portion adjacent to said concavely curved sidewall, said three holes being spaced along an arc that parallels said concavely curved sidewall, and said at least one hole further includes five holes in said central portion adjacent to said convexly curved sidewall, said five holes being spaced along an arc that parallels said convexly curved sidewall.

7. The plating system of claim 1, wherein said coupling member includes: a flange at a distal end of said coupling member, said flange defining a plane; a base extending proximally from said flange; a first arm and a second arm extending proximally from said base, said first and second arms located on opposite sides of a channel for receiving the connecting element, said first and second arms defining respective ones of a lateral side and a medial side of said coupling member with said channel opening at cephalad and caudal sides of said coupling member; and said transverse bore extends through said base and opens at said medial side and said lateral side of said coupling member, said transverse bore being isolated from said channel by said base.

8. The plating system of claim 7, wherein said transverse bore includes a proximal side toward said arms and a distal side toward said flange, said proximal and distal sides being elongated in a direction between said medial and lateral sides of said coupling member and elongated in a direction between said cephalad and caudal sides of said coupling member, wherein said mounting member is a cylindrical pin and said transverse bore is substantially greater in dimension in said direction between said cephalad and caudal sides of said coupling member than said cylindrical pin to allow said coupling member to rotate on said cylindrical pin in said plane and translate on said cylindrical pin transversely to said medial-lateral axis.

9. The plating system of claim 8, wherein said elongated slot and said cylindrical pin are substantially greater in length in said direction between said medial and lateral sides of said coupling member than said proximal and distal sides of said transverse bore in said direction between said medial and lateral sides of said coupling member to allow said coupling member to translate on said cylindrical pin along said medial-lateral axis.

10. The plating system of claim 1, wherein said coupling member is translatable on said mounting member relative to said at least one lateral portion along said medial-lateral axis between opposite sides of said elongated slot and said associated coupling member is further translatable by rotation on said mounting member in said elongated slot.

11. An occipital plating system, comprising:
a plate including a central portion extending along a medial-lateral axis between opposite first and second lateral portions, said plate further including a top surface and a bottom surface opposite said top surface, said bottom surface for positioning distally toward an occiput, said central portion of said plate including at least one fastener hole extending between said top and bottom surfaces to receive a fastener therethrough, said first and second lateral portions each including a coupling member associated therewith extending proximally from said top surface, said coupling members each being configured to engage a connecting element extending from a vertebra to the occiput, wherein:
said first and second lateral portions each include an elongated slot extending along said medial-lateral axis that opens at said top and bottom surfaces;
first and second mounting members are secured to respective ones of said first and second lateral portions, said first and second mounting member each extend across said elongated slot of said respective lateral portion in a direction along said medial-lateral axis;
said coupling members of said first and second lateral portions are positioned on said respective mounting member and each of said coupling members is translatable on said respective mounting member between opposite sides of said elongated slot;
said first and second mounting members each being an elongated pin extending across said elongated slot between opposite sides of said at least one lateral portion;
said coupling members include a channel for receiving the connecting element and a transverse bore extending through said coupling members that is isolated from said channel; and
said elongated pins are positioned through said transverse bore with said coupling members being slidable along said elongated pins and rotatable on said elongated pins.

12. The plating system of claim 11, wherein each of said coupling members includes: a flange at a distal end of said coupling member, said flange lying in a plane; a base extending proximally from said flange; a first arm and a second arm extending proximally from said base, said first and second arms located on opposite sides of a channel of said coupling member, said first and second arms defining respective ones of a lateral side and a medial side of said coupling member with said channel opening at cephalad and caudal sides of said coupling member; and said transverse bore extends through said base and opens at said medial side and said lateral side of said coupling member, said transverse bore being isolated from said channel by said base.

13. The plating system of claim 12, wherein said transverse bore includes a proximal side and a distal side, said proximal and distal sides each being elongated in a direction between said medial and lateral sides of said coupling member and elongated in a direction between said cephalad and caudal sides of said coupling member, wherein said transverse bore is substantially greater in dimension in said direction between said cephalad and caudal sides of said coupling member than said mounting member to allow said coupling member to translate on said mounting member transversely to said medial-lateral axis and to rotate on said mounting member in said plane.

14. The plating system of claim 13, wherein said elongated slot and said mounting member are substantially greater in length in said direction between said medial and lateral sides of said coupling member than said proximal and distal sides of said transverse bore in said direction between said medial and lateral sides of said coupling member to allow said coupling member to translate on said mounting member along said medial-lateral axis.

15. The plating system of claim 11, wherein said plate includes: a sidewall at a cephalad end of said plate that is convexly curved across said medial-lateral axis and extends between said top and bottom surfaces of said plate; a sidewall at a caudal end of said plate that is concavely curved across said medial lateral axis and extends between said top and bottom surfaces of said plate; and said lateral portions of said plate each include a convexly curved sidewall extending between said convexly curved sidewall and said concavely curved sidewall.

16. The plating system of claim 15, wherein: said top surface extends along said central portion of said plate and said lateral portions each include a second top surface that is spaced from said top surface of said central portion of said plate, said lateral portions each including a thickness between said bottom surface of said plate and said second top surface that is greater than a thickness of said central portion between said bottom surface of said plate and said top surface of said central portion; and said second top surfaces each form a circular shape at respective ends of said central portion when said plate is viewed in a direction from said top surface toward said bottom surface.

17. The plating system of claim 16, wherein said at least one hole includes three holes in said central portion adjacent to said concavely curved sidewall, said three holes being spaced along an arc that parallels said concavely curved sidewall, and said at least one hole includes five holes in said central portion adjacent to said convexly curved sidewall, said five holes being spaced along an arc that parallels said convexly curved sidewall.

18. The plating system of claim 11, wherein said coupling member is translatable on said mounting member and relative to said lateral portion along said medial-lateral axis between opposite sides of said elongated slot and said associated coupling member is further translatable by rotation on said mounting member in said elongated slot.

* * * * *